(12) United States Patent
Steib

(10) Patent No.: US 9,144,505 B2
(45) Date of Patent: Sep. 29, 2015

(54) INTERVERTEBRAL DISC PROSTHESIS AND INSTRUMENTATION FOR INSERTION OF THE PROSTHESIS BETWEEN THE VERTEBRAE

(71) Applicant: LDR Medical

(72) Inventor: Jean-Paul Steib, Strasbourg (FR)

(73) Assignee: LDR Medical, Rosieres Pres Troyes (FR)

( * ) Notice: Subject to any disclaimer, the term of this patent is extended or adjusted under 35 U.S.C. 154(b) by 0 days.

(21) Appl. No.: 14/325,317

(22) Filed: Jul. 7, 2014

(65) Prior Publication Data

US 2015/0025638 A1 Jan. 22, 2015

Related U.S. Application Data

(60) Continuation of application No. 13/620,797, filed on Sep. 15, 2012, now Pat. No. 8,771,284, which is a division of application No. 11/362,253, filed on Feb. 24, 2006.

(51) Int. Cl.
*A61F 2/00* (2006.01)
*A61B 17/58* (2006.01)
*A61B 17/60* (2006.01)
*A61F 2/44* (2006.01)
*A61F 2/46* (2006.01)
*A61F 2/30* (2006.01)

(52) U.S. Cl.
CPC ............. *A61F 2/4425* (2013.01); *A61F 2/4611* (2013.01); *A61F 2002/30235* (2013.01); *A61F 2002/30365* (2013.01); *A61F 2002/30369* (2013.01); *A61F 2002/30512* (2013.01); *A61F 2002/30601* (2013.01); *A61F 2002/30616* (2013.01); *A61F 2002/30649* (2013.01); *A61F 2002/30662* (2013.01); *A61F 2002/30841* (2013.01); *A61F 2002/30878* (2013.01); *A61F 2002/30884* (2013.01); *A61F 2002/30904* (2013.01); *A61F 2002/443* (2013.01); *A61F 2002/4622* (2013.01); *A61F 2002/4627* (2013.01); *A61F 2002/4628* (2013.01); *A61F 2220/0025* (2013.01); *A61F 2220/0033* (2013.01); *A61F 2230/0069* (2013.01); *Y10S 606/914* (2013.01)

(58) Field of Classification Search
USPC ............................... 623/17.11–17.16; 606/99
See application file for complete search history.

(56) References Cited

U.S. PATENT DOCUMENTS

2005/0125029 A1* 6/2005 Bernard et al. ............... 606/205
2005/0197706 A1* 9/2005 Hovorka et al. ........... 623/17.15

* cited by examiner

*Primary Examiner* — Sameh Boles
(74) *Attorney, Agent, or Firm* — Denko Coburn Lauff LLP

(57) ABSTRACT

The present invention relates to an intervertebral disc prosthesis and insertion instrumentation, the prosthesis comprising at least first and second osseous anchoring means, the first osseous anchoring means disposed proximal to the periphery of the plate on which it is situated and the second osseous anchoring means being offset along the antero-posterior axis, the second osseous anchoring means comprising a basal portion and a sharp-edged portion of width narrower than the basal portion. The instrumentation comprises a rod fitted with at least two feet forming a clip and sliding in a tube, sliding the rod in the tube, in the direction of the manipulation end, causing closing of the clip by contact between the exterior of the feet and a truncated portion of the tube and sliding the rod in the tube, in the direction of the prehension end, causing opening of the clip by contact between an axis and the interior of the feet of the rod.

2 Claims, 6 Drawing Sheets

FIG. 5A
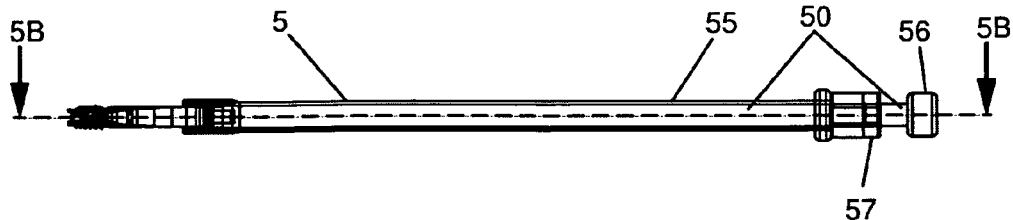
FIG. 5B
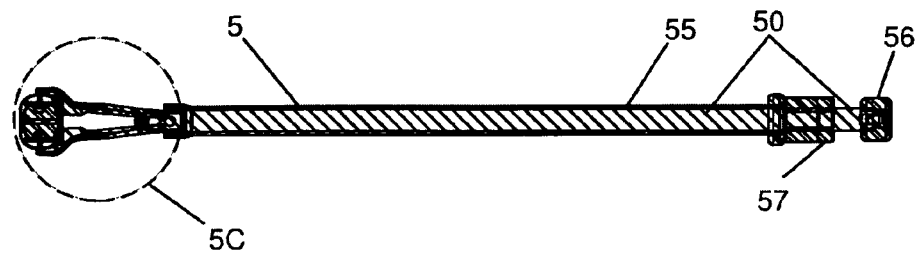
FIG. 5C
FIG. 5D
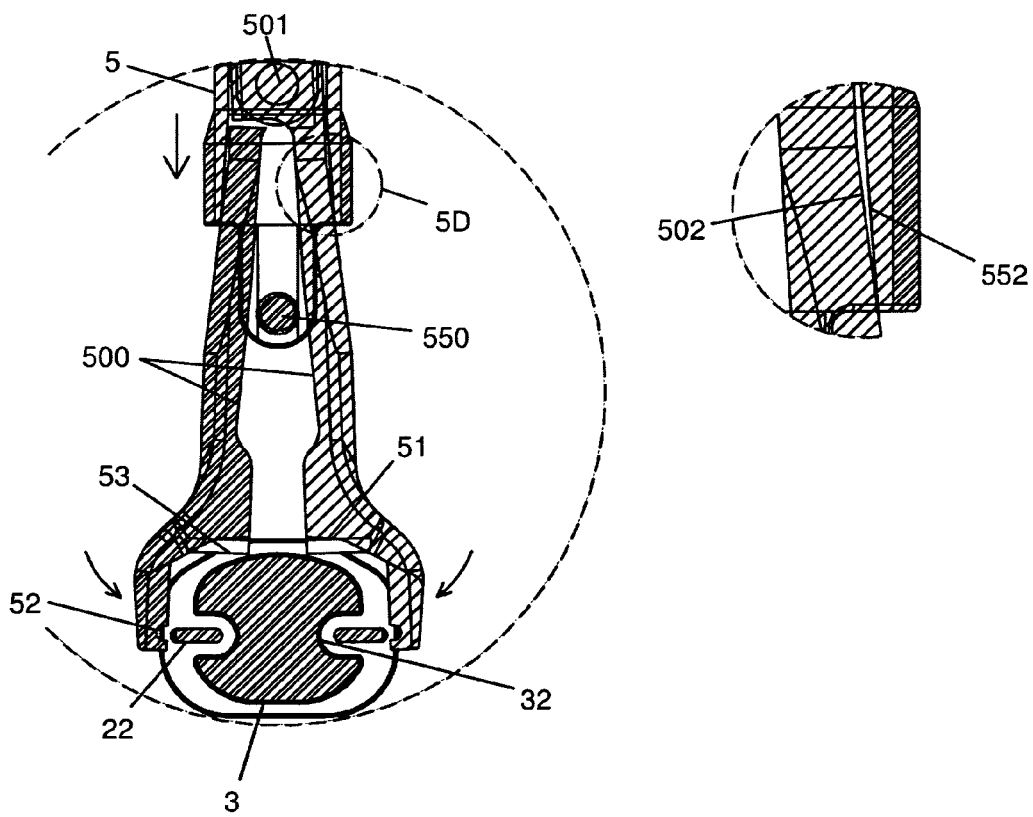

FIG. 6A
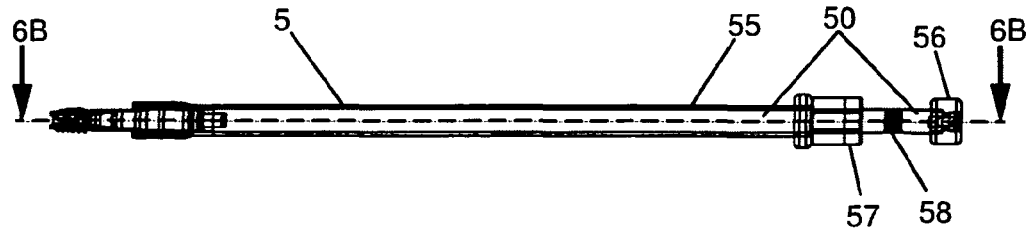
FIG. 6B
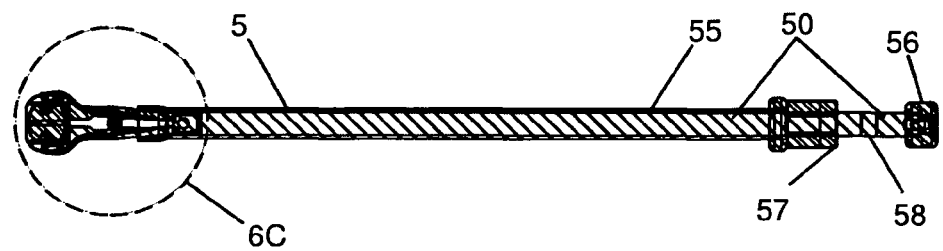
FIG. 6C
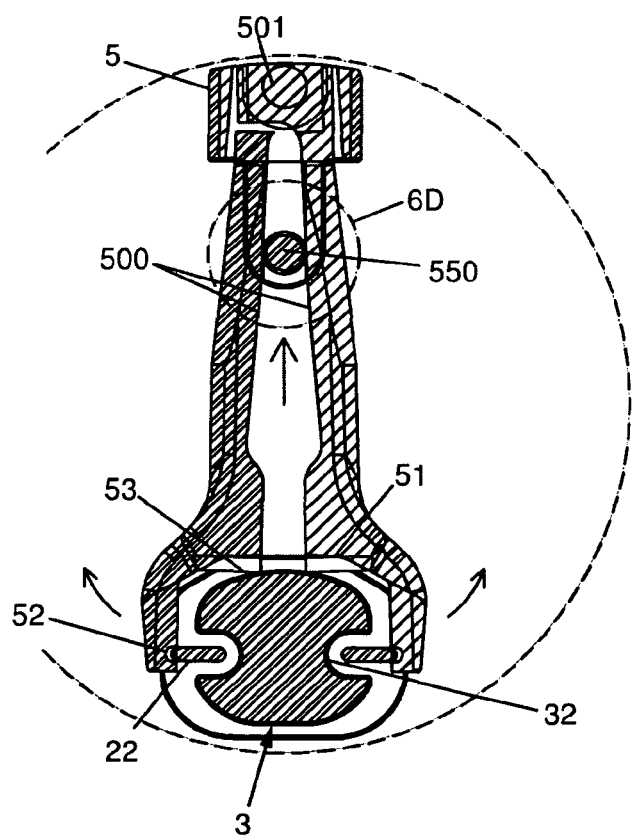
FIG. 6D

INTERVERTEBRAL DISC PROSTHESIS AND INSTRUMENTATION FOR INSERTION OF THE PROSTHESIS BETWEEN THE VERTEBRAE

CROSS REFERENCE TO RELATED APPLICATIONS

This application continuation of U.S. patent application Ser. No. 13/620,797 filed Sep. 15, 2012, and issuing as U.S. Pat. No. 8,771,284 on Jul. 8, 2014, which is a divisional of U.S. patent application Ser. No. 11/362,253 filed Feb. 24, 2006, which claims priority under 35 U.S.C. 119 to French Patent Application No. 05 12133, filed in FRANCE on Nov. 30, 2005.

BACKGROUND OF THE INVENTION

The present invention concerns an intervertebral disc prosthesis, intended to be substituted for fibro-cartilaginous discs ensuring connection between the vertebrae of the spinal column.

Various types of intervertebral disc prostheses are known in the prior art. Numerous prostheses, such as for example in the patent applications WO 02 089 701 and WO 2004/041129, are constituted by a lower plate and an upper plate forming a sort of cage articulated about a central core. Other prostheses such as those described in the U.S. Pat. No. 5,676,701 and in the patent application WO 03/059212 A1, for example, comprise only a lower plate and an upper plate articulated to one another by means of an articulation surface. The advantage of these two types of articulated prostheses is that they offer freedom of movement for the patient wearing the prosthesis, by enabling inclination and/or rotation of one of the plates relative to the other. The additional advantage of prostheses comprising a central core, mobile between the plates, is that they allow spontaneous positioning of the core in the ideal position to absorb the constraints imposed on the prosthesis. Some of the prostheses whereof the central core is mobile between the plates comprise cooperation means present on the core and on at least one of the plates to limit displacement of the core. In these prostheses described in the prior art, osseous anchoring means are likewise known which fix each of the plates of the prosthesis in each of the vertebrae between which the prosthesis is intended to be implanted. These osseous anchoring means can consist of fins intended to be fixed on the plates of the prosthesis and cooperate with a groove made in the surface of the vertebral plates or in anchors intended to be planted in the vertebral body.

However, the disadvantage of these prostheses is that they are not easy to insert between the vertebrae, since implantation requires good stability of the different elements of the prosthesis between one another. This stability is often missing in prostheses known from the prior art and the known instrumentation does not generally ensure stability of the elements of the prosthesis. In fact, the articulated plates of the prostheses possess degrees of liberty conferring comfort to the patient, but discomfort for the surgeon who fits them. The plates risk inclining and turning about their articulation surfaces. The surgeon is therefore not guaranteed that the elements are properly aligned in the antero-posterior axis of the vertebral column.

SUMMARY

In this context, it is interesting to propose a prosthesis and associated instrumentation enabling the prosthesis to be implanted between the vertebrae, while retaining the necessary alignment of the different elements of the prosthesis between one another. The aim of the present invention therefore is to eliminate certain disadvantages of the prior art by proposing an intervertebral disc prosthesis and instrumentation for insertion of the prosthesis between the vertebrae allowing the prosthesis to be implanted by following a defined axis.

This aim is attained by an intervertebral disc prosthesis comprising at least two plates, so-called first and second plates, articulated between one another by means of a curved surface, so-called articulation, of at least one of the plates, allowing pivoting and/or inclination of the plates relative to one another, by rotation about, respectively, an axis substantially perpendicular to the plane of the plates and an axis substantially in the plane of the plates, each of the plates comprising a so-called contact surface, intended to be made solid with a vertebral plate of one of the vertebrae between which the prosthesis is intended to be implanted, characterised in that the contact surface of at least one of the plates comprises at least first osseous anchoring means and at least second osseous anchoring means, the first osseous anchoring means extending to in the vicinity of the periphery of the plate on which it is situated and the second osseous anchoring means being offset according to the antero-posterior axis relative to the first osseous anchoring means, said second osseous anchoring means offset comprising a portion, so-called basal, solid with the plate on which it is situated and a portion, so-called sharp-edged, of width narrower than the basal portion and forming a guide blade intended to prevent rotation of the plates of the prosthesis between one another and facilitate insertion of the prosthesis.

In accordance with another specific characteristic, the second plate comprises a curved articulation surface whereof at least one part cooperates with a curved articulation surface of the first plate to which it is complementary, to allow pivoting and/or inclination of the plates relative to one another.

In accordance with another specific characteristic, the curved surface of the first plate is concave and the curved articulation surface of the second plate is convex.

In accordance with another specific characteristic, the curved surface of the first plate is convex and the curved articulation surface of the second plate is concave.

In accordance with another specific characteristic, it likewise comprises a core comprising a plane surface and a curved articulation surface and in that only the first plate comprises a curved articulation surface cooperating with at least one part of the curved surface of the core to which it is complementary, to allow pivoting and/or inclination of the plates relative to one another, the plane surface of the core cooperating with at least one part of a plane surface of the second plate to allow translation and/or rotation of the core relative to the second plate in at least one direction perpendicular to the vertical axis of the backbone, the second plate comprising cooperation means complementary to cooperation means of the core allowing at least this translation of the core to be limited or eliminated relative to the second plate.

In accordance with another specific characteristic, the curved surface of the first plate is concave and the curved surface of the core is convex.

In accordance with another specific characteristic, the curved surface of the first plate is convex and the curved surface of the core is concave.

In accordance with another specific characteristic, the first osseous anchoring means of the plates consist of at least one winglet located in the vicinity of the periphery of the plate and fitted with notches oriented so as to oppose withdrawal of the prosthesis from the discal space.

In accordance with another specific characteristic, the notches of the first osseous anchoring means are at a height increasing in the postero-anterior direction, such that the notches are at a height greater at the front than at the rear of the prosthesis and so that the insertion of the prosthesis in the discal space, in the antero-posterior direction of the vertebrae is facilitated by the notches attacking the osseous tissue not yet attacked by the preceding notches.

In accordance with another specific characteristic, at least the anterior edge of at least one of the plates of the prosthesis comprises 3 support faces whereof one leading face substantially perpendicular to the insertion axis of the prosthesis in the discal space and two antero-lateral faces each forming, in the plane of the plate, an angle with the anterior face and with one of the lateral edges of the plate, these 3 support faces allowing stabilising of the prosthesis during its insertion in the discal space by an instrument whereof at least a portion has a shape complementary to these 3 support faces.

In accordance with another specific characteristic, at least one of the plates has, at least on its posterior edge, at least one chamfer facilitating insertion of the prosthesis in the discal space.

In accordance with another specific characteristic, the second osseous anchoring means of the plates consists of at least one aileron located in the vicinity of an edge of the plate and oriented in the insertion axis of the prosthesis between the vertebrae.

In accordance with another specific characteristic, the aileron has a lesser height at its posterior end than at its anterior end, this difference in height imparting to the aileron an inclined profile facilitating its insertion in the discal space in the antero-posterior direction.

In accordance with another specific characteristic, at least one of the plates comprises at least one default form, such as a notch, allowing the fitting of the end of a prehension device to the prosthesis.

In accordance with another specific characteristic, the cooperation means of the second plate are male means located in the vicinity of the edges of the second plate and cooperating with female means of the core.

In accordance with another specific characteristic, the male cooperation means of the second plate are two studs located on the two lateral edges of the second plate and the female cooperation means of the core are two recesses made on the lateral edges of the core.

In accordance with another specific characteristic, the dimensions of each male cooperation means are slightly less than those of each female cooperation means so as to allow a slight clearance between the core and the second plate about the middle position of the core, corresponding to a centre of articulation of the prosthesis.

In accordance with another specific characteristic, the dimensions of each male cooperation means are substantially the same as those of each female cooperation means, so as to prevent any clearance between the core and the second plate and block the core in its middle position corresponding to a centre of articulation of the prosthesis.

In accordance with another specific characteristic, the cooperation means of the second plate are female means located in the vicinity of the edges of the second plate and cooperating with male means of the core.

In accordance with another specific characteristic, the dimensions of each male cooperation means are slightly less than those of each female cooperation means so as to allow slight clearance between the core and the second plate, about the middle position of the core, corresponding to a centre of articulation of the prosthesis.

In accordance with another specific characteristic, the dimensions of each male cooperation means are substantially the same as those of each female cooperation means so as to prevent any clearance between the core and the second plate and block the core at its middle position, corresponding to a centre of articulation of the prosthesis.

In accordance with another specific characteristic, the male cooperation means of the core are two studs located on the two lateral edges of the core and the female cooperation means of the second plate are four walls located, two by two, on each of the two lateral edges of the second plate.

In accordance with another specific characteristic, the female cooperation means of the second plate comprise a portion curved in to the centre of the plate and partially covering the male cooperation means of the core so as to prevent lifting of the core.

In accordance with another specific characteristic, the plane means representing the contact surfaces of the plates are substantially parallel or form an acute angle, the inclination obtained by such an angle allowing the overall form of the prosthesis to adapt to the anatomy of the backbone or optionally correct faults in inclination of the vertebrae of the patient for whom the prosthesis is intended.

In accordance with another specific characteristic, the same plates can be assembled with cores of different thicknesses and/or sizes and/or forms.

Another aim of the present invention is to eliminate certain disadvantages of the prior art by proposing instrumentation for insertion of an intervertebral disc prosthesis between the vertebrae allowing stability of the different elements of the prosthesis to be maintained between one another over the course of insertion of the latter between the vertebrae.

This aim is attained by insertion instrumentation of an intervertebral disc prosthesis between the vertebrae, comprising at least one prehension device for the prosthesis comprising a so-called manipulation end and a so-called prehension end, the prehension device being characterised in that it comprises a rod fitted, at the prehension end, with at least one axis of rotation on which are mounted at least two feet free in rotation about this axis, the ensemble of the rod and feet forming a clip mounted slidably in a hollow tube whereof the prehension end has an internal profile in a truncated form and comprises an axis perpendicular to the plane of the two feet of the clip, the ensemble formed by the two feet having a width, in the plane of the opening of the clip, greater than the width of the rod, the sliding of the rod in the tube, in the direction of the manipulation end, therefore causing closing of the clip by contact between the exterior of the feet and the truncated portion of the tube, the sliding of the rod in the tube, in the direction of the prehension end, causing opening of the clip by contact between the axis of the tube and the interior of the feet of the rod.

In accordance with another specific characteristic, the rod is fitted with a grip at the manipulation end, so as to allow the user to have the rod slide in the tube.

In accordance with another specific characteristic, the tube is fitted with a ring mobile in rotation relative to the tube and comprising a thread complementary to at least one threaded portion of the rod, the relative position of the thread of the ring and of the threading of the rod allowing blockage of the rod in the tube at least in the position where the clip is closed.

In accordance with another specific characteristic, the ends of the feet, at the level of the prehension end, each have at least one contact surface with at least an edge of an element of the prosthesis, imparting to the clip a profile adapted to the form of the prosthesis to be implanted.

In accordance with another specific characteristic, the profile adapted to the form of the prosthesis to be implanted consists of at least one contact surface with the leading edge of the prosthesis, at least one contact surface with the leading edge of a central core of the prosthesis and at least one contact surface with elements located on the lateral edges of the prosthesis.

In accordance with another specific characteristic, at least one contact surface with elements located on the lateral edges of the prosthesis consists of prehension means of cooperation means between the core and a plate of the prosthesis.

In accordance with another specific characteristic, at least one contact surface with elements located on the lateral edges of the prosthesis consists of cooperation means with a default form of at least one of the plates of the prosthesis.

In accordance with another specific characteristic, the profile adapted to the form of the prosthesis to be implanted consists of at least the contact surface with the leading edge of the prosthesis comprising 3 support faces complementary to 3 support faces present at least on the leading edge of at least one of the plates of the prosthesis, these 3 support faces comprising a leading face substantially perpendicular to the insertion axis of the prosthesis in the discal space and two antero-lateral faces each forming, in the plane of the plate, an angle with the leading face and with one of the lateral edges of the plate, the cooperation between this instrumentation profile and these 3 faces of the prosthesis allowing the latter to be stabilised during its insertion in the discal space.

BRIEF DESCRIPTION OF THE DRAWINGS

Other specific characteristics and advantages of the present invention will emerge more clearly from reading the description hereinbelow, given in reference to the attached diagrams, in which:

FIGS. 5A, 5B illustrate, respectively, a profile view with a cutting plane of FIG. 5C and a sectional view according to this plane, of a prehension device of a prosthesis according to an embodiment of the invention when the device is in the open position and does not lock in the prosthesis, FIGS. 5C and 5D representing a detail, respectively of the part 5C enclosed in FIG. 5B and of the part 5D enclosed in FIG. 5C, FIGS. 6A, 6B illustrate, respectively, a profile view with a cutting plane of FIG. 6B and a sectional view according to this plane, of a prehension device of a prosthesis according to an embodiment of the invention when the device is in the closed position and locks in the prosthesis, FIGS. 6C and 6D representing a detail, respectively of the enclosed part 6C in FIG. 6B and of the enclosed part 6D in FIG. 6C.

DETAILED DESCRIPTION OF THE EMBODIMENTS

Figure 1A:
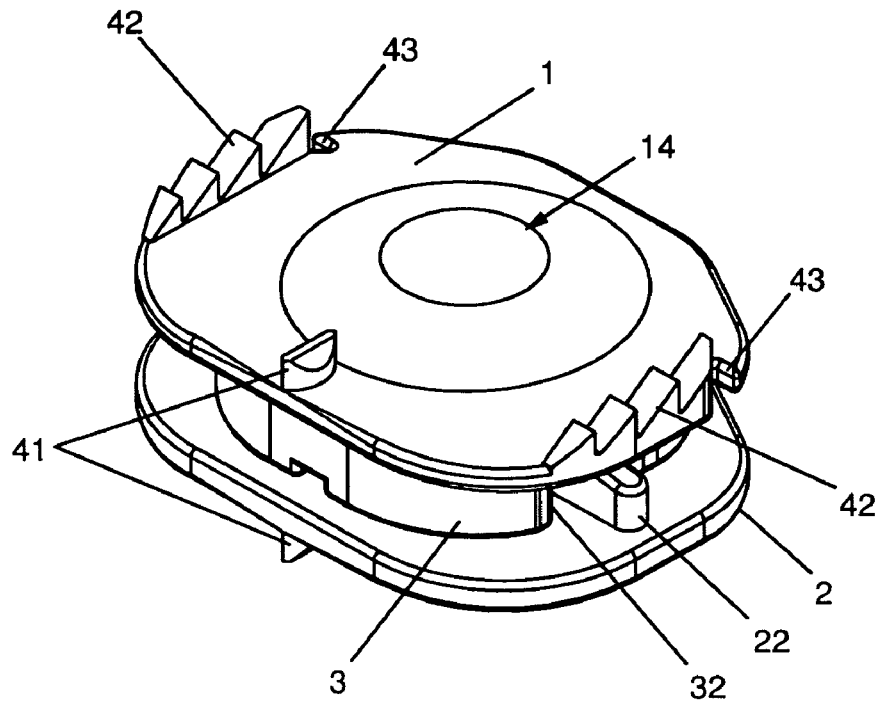
FIGS. 1A and 1B illustrate plan views in perspectives and, respectively, rear views and front views, of an intervertebral disc prosthesis according to an embodiment of the invention.
Figure 1B:
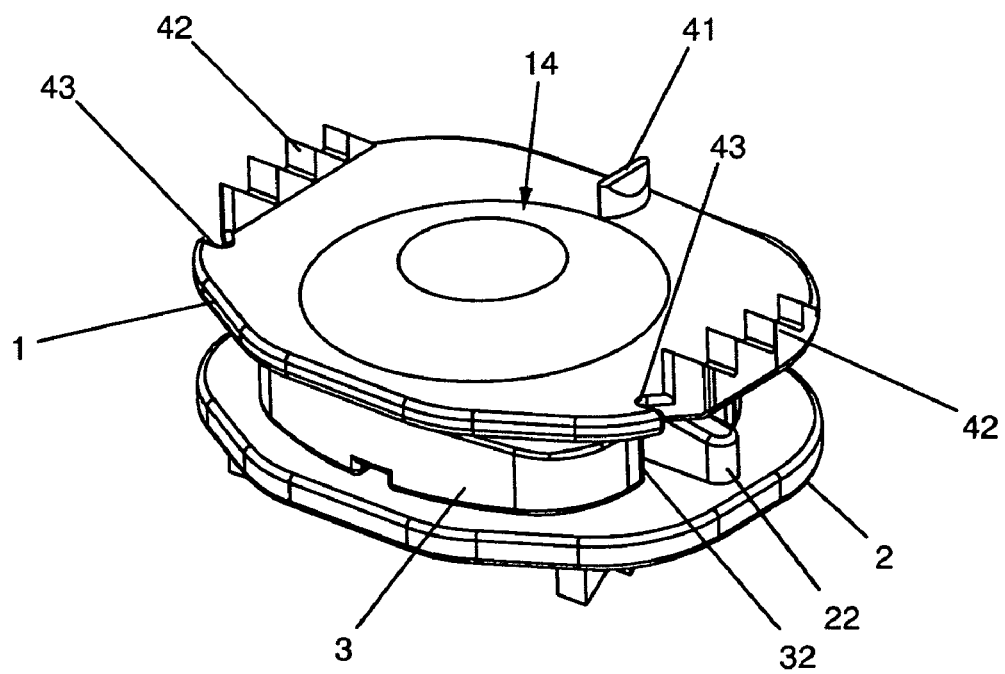
Figure 2A:
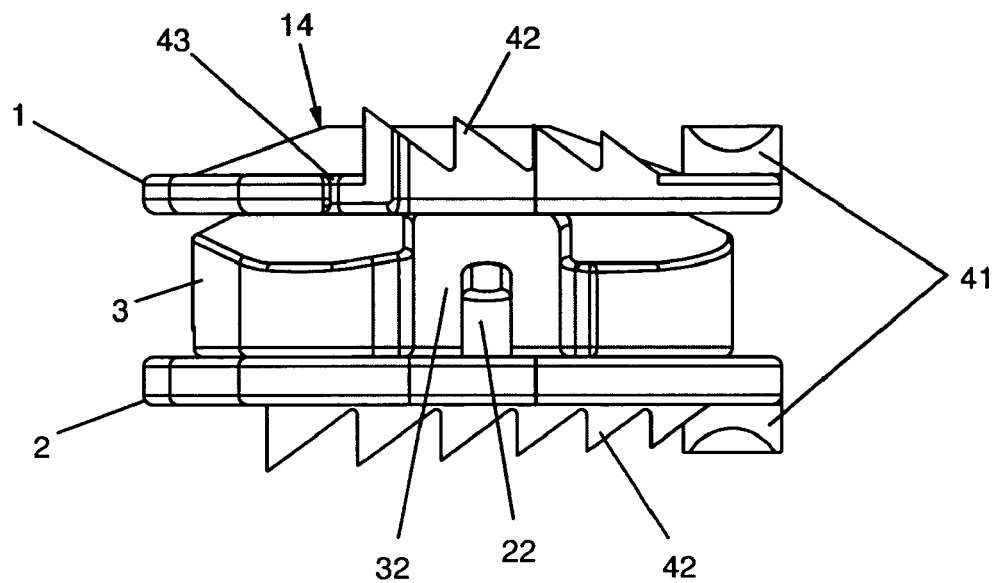
FIGS. 2A and 2B illustrate, respectively, a profile view and a rear view of an intervertebral disc prosthesis according to an embodiment of the invention.
Figure 2B:
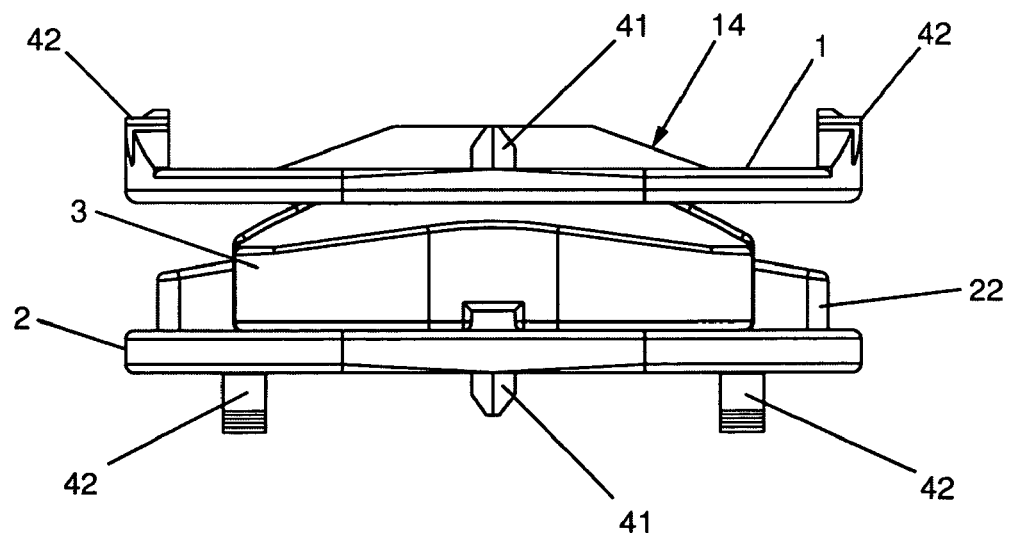

The present invention relates to an intervertebral disc prosthesis comprising at least osseous anchoring means (41) forming a guide blade intended to prevent rotation of the plates of the prosthesis between one another and facilitate insertion of the prosthesis. More precisely, the prosthesis comprises at least first osseous anchoring means (42) and at least second osseous anchoring means (41), the first osseous anchoring means (42) extending to near the periphery of the plate on which it is situated and the second osseous anchoring means (41) being offset according to the antero-posterior axis relative to the first osseous anchoring means (42). The second offset osseous anchoring means (41) comprise a portion, so-called basal, solid with the plate on which it is situated and a portion, so-called sharp-edged, of width narrower than the basal portion. This sharp-edged portion forms a sort of blade intended to score the surfaces of the vertebral plates with which it comes into contact during implantation of the prosthesis and this blade then naturally forms a guide rail in the vertebra, thus preventing any displacement of the elements of the prosthesis between one another. In the various embodiments described hereinbelow, the prosthesis comprises at least two plates (1 and 2), so-called first (1) and second (2) plates, articulated between one another by means of a curved surface, so-called articulation surface, of at least one of the plates. This curved articulation surface allows pivoting of the plates (1, 2) relative to one another, by rotation about an axis substantially perpendicular to the plane of the plates and/or inclination of the plates (1, 2) relative to one another, by rotation about an axis substantially in the plane of the plates (1, 2). Each of the plates (1, 2) comprises a so-called contact surface intended to be made solid with a vertebral plate of one of the vertebrae between which the prosthesis is intended to be implanted. As is particularly evident in the embodiment illustrated in FIGS. 1A to 3C, the contact surface of the first plate (1) comprises a bulged portion (14) matching the form of the surface of the lower plate of a vertebra. The prostheses according to the present invention could comprise only two plates articulated between one another by means of a curved surface (not illustrated) or two plates (1, 2) articulated between one another by means of a central mobile core (3) having a curved surface cooperating with at least one part of a curved surface of one of the plates and a plane surface cooperating with at least one part of a plane surface of the other plate, as shown in FIGS. 1A to 2B.

In this illustrated embodiment, the first plate (1) comprises a curved articulation surface and this surface cooperates with at least one part of the curved surface of the core (3) to which it is complementary, to allow pivoting and/or inclination of the plates (1, 2) relative to one another. The plane surface of the core (3) cooperates with at least one part of a plane surface of the second plate (2) to allow translation of the core (3) relative to the second plate (2) in at least one direction perpendicular to the vertical axis of the spinal column and/or rotation of the core (3) relative to the second plate (2) by rotation about an axis substantially perpendicular to the plane of these plane surfaces. In the embodiments illustrated in the figures, the curved surface of the first plate (1) is concave and the curved surface of the core (3) is convex, but it could eventuate that the curved surface of the first plate (1) is convex and the curved surface of the core (3) is concave.

The second plate (2) comprises cooperation means (22) complementary to cooperation means (32) of the core (3) so as to limit or cancel at least this translation of the core (3) relative to the second plate (2). In the embodiments illustrated in the figures, the cooperation means (22) of the second plate (2) are male means located in the vicinity of the edges of the second plate (2) and cooperating with female means (32) of the core (3). In the embodiments illustrated in the figures, these male cooperation means (22) of the second plate (2) are two studs located on the two lateral edges of the second plate (2) and the female cooperation means (32) of the core (3) are two recesses made on the lateral edges of the core (3). In other possible embodiments not illustrated here, these cooperation means (32) of the core (3) can be male means consisting, for example, of two studs located on the two lateral edges of the core (3) and the cooperation means (22) of the second plate (2) can thus be female means consisting, for example, of four walls located, two by two, on each of the two lateral edges of the second plate (2). In these two embodiments, the cooperation means (22) of the second plate (2) can comprise a portion curved in towards the centre of the plate (2) and partially covering the cooperation means (32) of the core (3) so as to prevent lifting of the core (3). In an embodiment according to the present invention the dimensions of each male cooperation means (32, 22) could be slightly less than those of each female cooperation means (22, 32) so as to allow slight clearance between the core (3) and the second plate (2) about the middle position of the core (3) relative to the plates (1, 2), this middle position corresponding to a centre of articulation of the prosthesis. In another embodiment, the dimensions of each male cooperation means (32, 22) could be substantially identical to those of each female cooperation means (22, 32) so as to prevent any clearance between the core (3) and the second plate (2) and block the core (3) in its middle position corresponding to the centre of articulation. It can be interesting that the prosthesis according to the present invention can correct faults in inclination of the vertebrae between which it is intended to be implanted. In accordance with the desired result, this centre of articulation could have been provided to be at the centre of the prosthesis or be offset in at least one direction perpendicular to the axis of the spinal column. Similarly, the planes means representing the contact surfaces (14) of the plates (1, 2) could therefore be substantially parallel or form an acute angle. The inclination obtained by such an angle will allow the overall form of the prosthesis to adapt to the anatomy of the spinal column or optionally correct faults in inclination of the vertebrae of the patient for whom the prosthesis is intended. The same plates (1, 2) can be assembled with core (3) of different thicknesses and/or sizes and/or forms.

The prosthesis according to the present invention comprises osseous anchoring means ensuring good stability of the elements of the prosthesis between one another during implantation of the prosthesis between the vertebrae. For this, the prosthesis according to the present invention comprises at least first osseous anchoring means (42) and at least second osseous anchoring means (41). The first osseous anchoring means (42) extend to near the periphery of the plate on which it is situated and the second osseous anchoring means (41) is offset according to the antero-posterior axis relative to the first osseous anchoring means (42). Therefore, the first osseous anchoring means (42) could consist, in an embodiment not illustrated here, of a winglet oriented perpendicularly to the antero-posterior axis of the spinal column and located near the leading edge or posterior edge of the plate on which they are located. The second osseous anchoring means (41) will thus be located in the vicinity of the edge, respectively, trailing or leading. In the embodiment illustrated on FIGS. 1A to 4C, the first osseous anchoring means (42) consist of two winglets oriented as per the antero-posterior axis of the spinal column and located in the vicinity of the lateral edges of the plate on which they are found. These lateral winglets could have a length less than that of the plate and the second osseous anchoring means (41) could then be located in the vicinity of one of the trailing or leading edges of the plate. In these two embodiments, each of the winglets could be fitted with notches oriented so as to oppose withdrawal of the prosthesis from the discal space. In a variant embodiment, the notches of the first osseous anchoring means (42) are at a height increasing in the postero-anterior direction, as is particularly evident in FIG. 4C. More precisely, the notches are at a greater height at the front than at the rear of the prosthesis. Thus, during insertion, in the discal space, of the prosthesis in the antero-posterior direction of the vertebrae, each notch of the winglets attacks the osseous tissue not yet attacked by the preceding notch, thereby facilitating the insertion of the prosthesis in the discal space. The second offset osseous anchoring means (41) comprise a portion, so-called basal, solid with the plate on which it is situated and a portion, so-called sharp-edged, of a width narrower than the basal portion and forming a guide blade intended to prevent rotation of the plates of the prosthesis between one another and facilitate insertion of the prosthesis. This sharp-edged portion could be obtained, for example, due to at least one chamfer made on at least one of the lateral surfaces of the second osseous anchoring means (41). This second osseous anchoring means (41) could therefore consist, for example, of at least one aileron (41) or fin located in the vicinity of an edge of the plate and oriented in the insertion axis of the prosthesis between the vertebrae. Of course, two ailerons or fins could be provided to further still stabilise the prosthesis, even though the role of the aileron is more important on the posterior edge of the prosthesis, because the prosthesis is generally implanted along an antero-posterior pathway through the discal space between two adjacent vertebrae of the spinal column and this posterior edge is thus the first to be inserted in the discal space. In a variant embodiment, the aileron or fin could have a height less important at its posterior end than at its anterior end. Just as for the increasing height of the notches of the winglets, this difference in height of the aileron (41) gives it an inclined profile facilitating its insertion in the discal space in the antero-posterior direction. In addition, at least one of the plates (1, 2) of the prosthesis according to the present invention could, in an embodiment, comprise, at least on its trailing edge, at least one chamfer facilitating insertion of the prosthesis in the discal space.

Figure 3A:
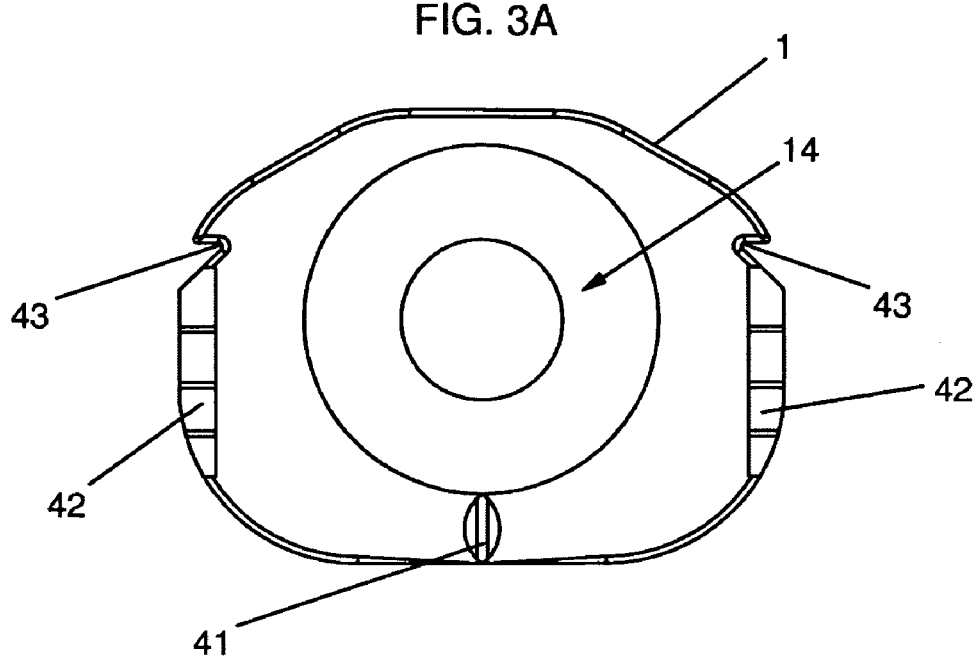
FIGS. 3A, 3B and 3C illustrate, respectively, a plan view, a rear view and a profile view of a first plate of an intervertebral disc prosthesis according to an embodiment of the invention.
Figure 3B:
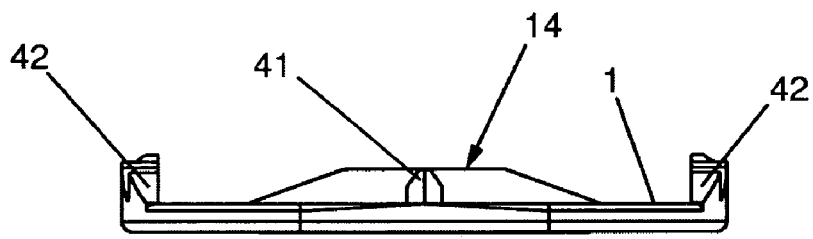
Figure 3C:
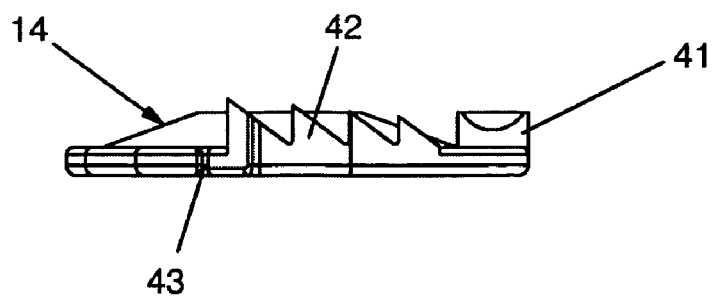
Figure 4A:
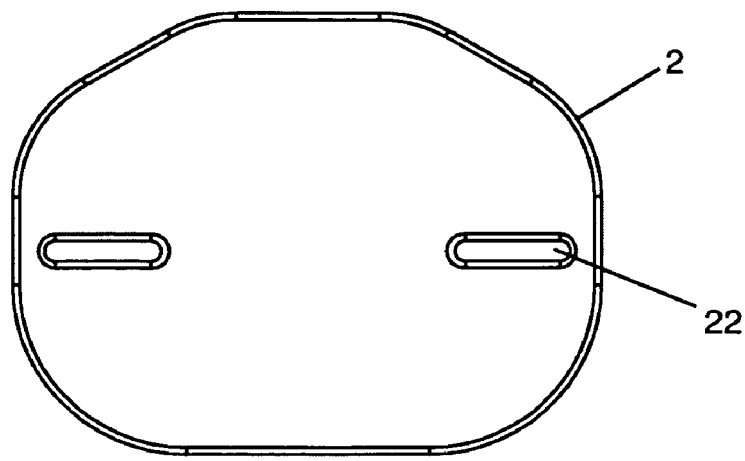
FIGS. 4A, 4B and 4C illustrate, respectively, a plan view, a rear view and a profile view of a second plate of an intervertebral disc prosthesis according to an embodiment of the invention.
Figure 4B:
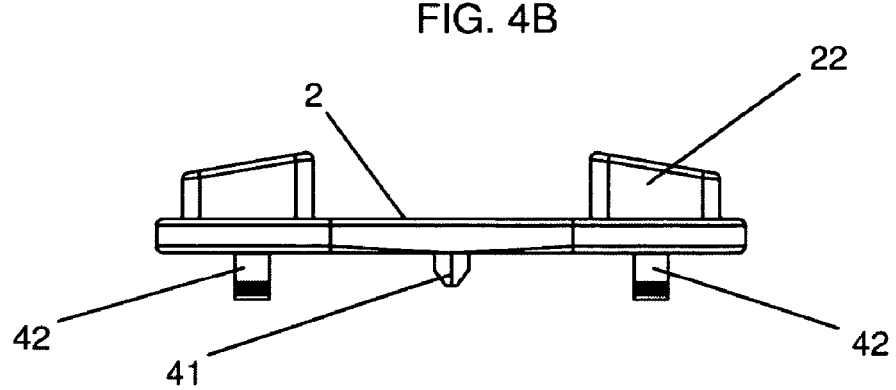
Figure 4C:
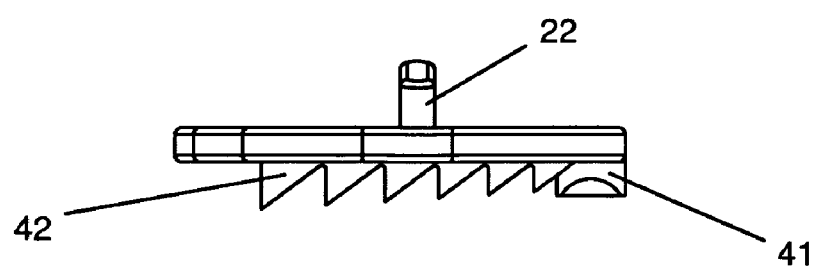

In an embodiment of the invention, at least the leading edge of at least one of the plates (1, 2) of the prosthesis could comprise 3 support faces, as is particularly evident in FIGS. 3A and 4A. These 3 faces consist of a leading face substantially perpendicular to the insertion axis of the prosthesis in the discal space and two antero-lateral faces each forming, in the plane of the plate, an angle with the leading face and with one of the lateral edges of the plate. Instead of presenting a rounded leading face, the prosthesis equipped with these 3 support faces is easy to stabilise during its insertion in the discal space, for example by means of an instrument whereof at least one portion has a form complementary to these 3 support faces. As is particularly evident in FIGS. 1A, 1B, 2A, 3A and 3C, at least one of the plates (1, 2) could comprise at least a default form (43), such as a notch, allowing the fitting of the end of a prehension device (5) of the prosthesis.

The invention further relates to instrumentation allowing insertion of the prosthesis between the vertebrae, ensuring good stability of the different elements of the prosthesis between one another during implantation. Such instrumentation according to the present invention comprises at least a prehension device (5) of the prosthesis, comprising a so-called manipulation end and a so-called prehension end. This prehension device (5) comprises a rod (50) fitted, at the prehension end, with at least an axis of rotation (501) on which are mounted at least two feet (500) free in rotation about this axis (501). The ensemble of the rod (50) and feet (500) forms a clip mounted slidably in a hollow tube (55) whereof the prehension end has an internal profile of truncated shape. The ensemble formed by the two feet (500) have a width, in the plane of the opening of the clip, greater than the width of the rod (50), so as to cooperate with the truncated portion of the hollow tube (55). The tube (55) comprises an axis (550) perpendicular to the plane of the two feet (500) of the clip and located between the two feet, so as to cooperate with the latter. The sliding of the rod (50) in the tube (55), in the direction of the manipulation end, therefore causes closing of the clip by contact between the exterior of the feet (500) and the truncated portion of the tube (55), while the sliding of the rod (50) in the tube (55), in the direction of the prehension end, causes opening of the clip by contact between the axis (550) of the tube (55) and the interior of the feet (500) of the rod (50). The rod (50) could be fitted with a grip (56) at the manipulation end, so as to allow the user to have the rod (50) slide in the tube (55). Also, this grip could be utilised to force insertion of the prosthesis in the discal space, for example, by striking on the grip by means of a tool such as a hammer, for example. The tube (55) could, in an embodiment of the invention, be fitted with a ring (57) mobile in rotation relative to the tube (55) and comprising a thread complementary to at least one threaded portion (58) of the rod (50). The relative position of the thread of the ring (57) and of the threading (58) of the rod (50) shall allow blockage of the rod (50) in the tube (55) at least in the position where the clip is closed. So, use of the prehension device (5) will help secure the clip on the prosthesis, for example while the surgeon strikes on the grip to insert the prosthesis in the discal space.

In the embodiment illustrated on the figures, the ends of the feet (500), at the level of the prehension end, each have at least one contact surface (51, 52, 53) with at least an edge of an element of the prosthesis, imparting to the clip a profile adapted to the form of the prosthesis to be implanted. This profile adapted to the form of the prosthesis to be implanted could consist of at least one contact surface (51) with the leading edge of the prosthesis, at least one contact surface (53) with the leading edge of a central core of the prosthesis and at least one contact surface (52) with elements located on the lateral edges of the prosthesis. In the case where the prosthesis comprises a central core fitted with cooperation means cooperating with cooperation means of at least one of the plates, the contact surface (52) with elements located on the lateral edges of the prosthesis could thus consist of prehension means of at least one of the cooperation means between the core (3) and a plate (1, 2) of the prosthesis. In the same way, in the case where the prosthesis comprises a plate having a default form (43), such as a notch, the contact surface (52) with elements located on the lateral edges of the prosthesis could consist of cooperation means with this default form (43). Also, the instrumentation according to the invention could be provided to cooperate perfectly with the different variant embodiments of the prosthesis according to the present invention and comprise a profile even more adapted to the form of the prosthesis. In particular, the contact surface (51) with the leading edge of the prosthesis, as well as optionally other surfaces, could comprise 3 support faces complementary to 3 support faces present at least on the leading edge of at least one of the plates (1, 2) of the prosthesis. These 3 support faces placed in complementary fashion to those of the prosthesis, then comprise a leading face substantially perpendicular to the insertion axis of the prosthesis in the discal space and two antero-lateral faces each forming, in the plane of the plate, an angle with the leading face and with one of the lateral edges of the plate. Cooperation between this instrumentation profile and these 3 faces of the prosthesis will help stabilise the latter during its insertion in the discal space, for example by preventing its rotation.

It must be evident for those skilled in the art that the present invention allows embodiments in numerous other specific forms without departing from the field of application of the invention as claimed. Consequently, the present embodiments must be considered by way of illustration, though they can be modified in the field defined by the reach of the attached claims, and the invention does not have to be limited to the details specified hereinabove.

The invention claimed is:

1. A combination comprising:
an intervertebral disc prosthesis for implantation between vertebrae of a spinal column along an insertion axis, the prosthesis comprising:
  a first plate and a second plate, each comprising leading and trailing edges and two lateral edges, with the first plate having a curved plate articulation surface and the second plate having a planar plate translation surface;
  a core having a curved core articulation surface and a planar core translation surface, the core configured for at least a portion of the curved core articulation surface to cooperate with at least a portion of the curved plate articulation surface to allow pivoting or inclination of the first plate and the second plate relative to one another, and at least a portion of the planar core translation surface to cooperate with at least a portion of the planar plate translation surface to allow translation or rotation of the core relative to the second plate in at least one direction; and
  at least two recesses disposed along opposite edges of the core, each recess configured to receive one of at least two studs disposed on the first or second plate proximal to lateral edges of the plate and configured to limit translation of the core with respect to the second plate, with each stud configured to extend outside the edge of the core to allow the studs to be grasped by an insertion instrument to hold the plate during insertion of the prosthesis; and
an insertion instrument for inserting the intervertebral disc prosthesis between vertebrae of a spinal column along an insertion axis, the instrument comprising feet rotatable about an axis of rotation, the feet collectively forming a clip for grasping the intervertebral disc prosthesis, the clip having a pair of recesses each configured to envelope an end of one of the studs and grasp the stud with the clip configured in a closed configuration.

2. The combination of claim 1 in which the trailing edges of the plates and a trailing edge of the core each has a support profile, and the instrument comprises complementary support profiles configured to support the intervertebral prosthesis and maintain orientation of the intervertebral prosthesis along the insertion axis during implantation of the intervertebral prosthesis.

* * * * *